(12) United States Patent
Kuppert et al.

(10) Patent No.: US 8,076,440 B2
(45) Date of Patent: Dec. 13, 2011

(54) POLYSILOXANE BLOCK COPOLYMERS

(75) Inventors: Dirk Kuppert, Recklinghausen (DE);
Burghard Grüning, Essen (DE); Brian Yang, Midlothian, VA (US); Sven Balk, Hanau (DE); Gerd Löhden, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 693 days.

(21) Appl. No.: 12/238,596

(22) Filed: Sep. 26, 2008

(65) Prior Publication Data

US 2009/0087399 A1  Apr. 2, 2009

Related U.S. Application Data

(60) Provisional application No. 60/975,574, filed on Sep. 27, 2007.

(51) Int. Cl.
*C08G 77/442* (2006.01)

(52) U.S. Cl. ......... 528/25; 525/343; 525/350; 526/75; 526/82; 526/90; 526/95; 526/126; 526/172; 526/319

(58) Field of Classification Search .............. None
See application file for complete search history.

(56) References Cited

U.S. PATENT DOCUMENTS

| | | |
|---|---|---|
| 4,968,750 A | 11/1990 | Eichenauer et al. |
| 5,202,190 A | 4/1993 | Kantner et al. |
| 6,143,848 A * | 11/2000 | Lee et al. .............. 526/212 |
| 6,858,696 B2 | 2/2005 | Destarac et al. |
| 7,230,051 B2 | 6/2007 | Gobelt et al. |

FOREIGN PATENT DOCUMENTS

| | | |
|---|---|---|
| EP | 0 582 152 | 2/1994 |
| EP | 1 375 605 | 1/2004 |
| JP | 3091509 | 4/1991 |

OTHER PUBLICATIONS

"Atom Transfer Radical Poymerization of (Meth)acrylates from Poly(dimethylsiloxane) Macroinitiators" authored by Matyjaszewski et al. and published in Macromolecules 1999, 32, 8760-8767.*

"End Group Modification or Poly(butyl acrylate) Prepared by Atom Transfer Radical Polymerization: Mechanistic Study using Gradient Polymer Elution Chromatography" authored by Snijder et al. and published in the Journal of Polymer Science, Part A: Polymer Chemistry (2202) 40, 2350-2359.*

Written Opinion of the PCT International Searching Authority.

* cited by examiner

*Primary Examiner* — Marc Zimmer
(74) *Attorney, Agent, or Firm* — Frommer Lawrence & Haug LLP

(57) ABSTRACT

The invention relates to polysiloxane block copolymers of the formula $A[LB(S)Q]_m$, where A is a polysiloxane block, L is a divalent organic linker, B is a polymer block composed of radically polymerizable monomers, S is a sulfur atom and Q is a monovalent organic radical and m is an integer from 1 to 50, to a method for their production, and to their use in cosmetics or personal care.

14 Claims, No Drawings

POLYSILOXANE BLOCK COPOLYMERS

This application claims benefit under 35 U.S.C. 119(e) of U.S. Provisional Application Ser. No. 60/975,574, filed on 27 Sep. 2007.

Any foregoing applications, including U.S. Provisional Application Ser. No. 60/975,574, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

The invention relates to polysiloxane block copolymers, in particular those which are suitable for use in cosmetic formulations and formulations for personal care. The invention further relates to the production of the polysiloxane block copolymers by atom transfer radical polymerization (referred to below for short as ATRP) and to the production of the corresponding formulations comprising the polysiloxane block copolymers, and also to their use in cosmetic and personal care applications.

A very particular aspect of the present invention is that polysiloxane-containing copolymers are produced and used whose terminal halogen atoms have been removed by adding a reagent, where optionally a functionalization of the polymer termini can be achieved. At the same time as removing the terminal halogen atoms, removal of the transition metal compounds by means of precipitation also takes place in a simultaneous process step, which permits simple removal of the transition metal compound from the reaction product.

Cosmetic and personal care formulations, such as, for example, hairstyling sprays, hair conditioners, foams, gels and shampoos, often comprise resins, gum and adhesive polymers in order to generate a large number of advantageous effects, such as, for example, film-forming properties, thickening properties, perceptible properties, such as improved feel, and hair-shaping properties.

Polymers which are used in such formulations are, inter alia, but not exclusively, organic or silicone-containing linear or grafted copolymers which may be composed of a large number of different monomers. Here, the polymer blocks may be alternating, random, blockwise arranged, branched or hyperbranched or homopolymer blocks.

Grafted polymers are known as film-forming polymers in cosmetic formulations for treating hair or skin. These grafted polymers typically comprise a polymeric backbone and one or more macromonomers grafted onto the backbone, through which it is possible to adjust the physical and chemical properties, such as, for example, the glass transition temperature and the solubility in water, independently of one another for the polymeric backbone and the grafted macromonomers in order to establish the desired overall properties of the complete polymer.

The specifications WO95/01383 (U.S. Pat. No. 5,730,966) and WO95/01384 disclose the use of water and alcohol soluble or dispersible grafted copolymers in hair and skincare compositions in which the copolymer has a backbone and one or more polymeric sidechains, produced by the random copolymerization of monomer A and monomer B. Monomer A is selected such that it has a hydrophobic character and macromonomer B has a long hydrophilic moiety. EP 0 412 704 (U.S. Pat. No. 5,618,524), EP 0 408 313 (U.S. Pat. No. 5,124,121) and EP 0 412 707 disclose the use of silicone grafted acrylate copolymers in haircare applications. U.S. Pat. No. 4,988,506 describes the use of grafted polysiloxane copolymers in haircare applications.

Block copolymers have the advantage over grafted copolymers that the polymer composition can be better controlled. This is particularly decisive and important if the desire is to tailor polymers with regions which have specific physical and chemical properties, e.g. alternating "hard" and "soft" segments in a polymer for hairspray applications provide improved hold and haptic properties.

U.S. Pat. No. 5,468,477 discloses cosmetic compositions comprising a vinyl-silicones grafted copolymer or a block copolymer wherein the copolymer comprises a silicone segment and a vinyl polymer segment. The block or grafted copolymer is produced by free radical polymerization of a mercapto-functionalized silicone, which functions as chain transfer agent, with a vinylic monomer. Polymers prepared by this method generally have low molecular weights and a low silicone content due to the premature chain termination reactions. Intramolecular crosslinking reactions additionally lead to an uncontrolled polymer composition.

Polydisperse systems with a mixture of chain lengths and various molecular architectures are thus obtained.

An alternative approach for the synthesis of block copolymers is the use of organopolysiloxane macroinitiators. These are organopolysiloxanes which contain groups which can form radicals. Such compounds are described in U.S. Pat. No. 5,523,365. The use for the production of copolymers is disclosed in WO 98/48771 and U.S. Pat. No. 6,074,628. A disadvantage of this method is working with hazardous organosiloxane microinitiators that have a tendency toward explosive decomposition, which have to be used in significant amounts, otherwise the end product contains too few silicone units. Furthermore, the industrial production of the macroinitiators is extremely difficult and associated with considerable safety expenditure. Moreover, the reaction is inefficient since large amounts of unreacted silicone oil have to be separated off by means of a time-consuming extraction. This process is only upscaleable with a high degree of difficulty.

WO 00/71606 (U.S. Patent Application Publication 2002-098214) describes a process for the production of polysiloxane block copolymers in which an organopolysiloxane macroinitiator is used in an atom transfer radical polymerization (ATRP) with copper salts as catalyst for producing block copolymers with controlled architecture. Their use in cosmetic and personal care compositions, in particular in formulations for the treatment of hair, is described. However, the specification discloses nothing about the copper content of the produced polymers. Moreover, the produced polymers are terminated with bromine atoms.

ATRP is a diverse method for synthesizing a large number of polymers and copolymers, such as, for example, polyacrylates, polymethacrylates, polystyrenes or copolymers. The ATRP method was developed in the 1990s primarily by Prof. Matyjaszewski and is described, inter alia, in *J. Am. Chem. Soc.*, 1995, 117, p. 5614 and WO 97/18247 (U.S. Pat. No. 5,763,548). A particular advantage of ATRP is that both the molecular weight and also the molecular weight distribution can be controlled. Being a living polymerization, it also permits the targeted construction of polymer architectures such as, for example, random copolymers and also block copolymer structures. By means of appropriate initiators, unusual block copolymers and star polymers, for example, are also accessible. Theoretical principles regarding the polymerization mechanism are explained, inter alia, in Hans Georg Elias, Makromolekule [Macromolecules], Volume 1, 6th Edition, Weinheim 1999, p. 344.

The ATRP process is based on a redox equilibrium between the growing radical polymer chain present only in a low concentration and a transition metal compound in a higher oxidation state (e.g. copper II) and the sleeping, preferably present combination of the polymer chain terminated with a halogen or a pseudo halogen and the corresponding transition metal compound in a lower oxidation stage (e.g. copper I). This is true both for the ATRP in the actual form, which is initiated with appropriately (pseudo) halogen substituted initiators, and also for reverse ATRP, in which the halogen is only bonded to the polymer chain upon establishing the equilibrium.

Irrespective of the method chosen, after the reaction has been terminated, the halogen atom always remains on the respective chain ends. However, the retention of this organically bonded halogen, in particular of organically bonded bromine, is disadvantageous for using polymers produced by the ATRP method in cosmetic and/or personal care formulations. Halogen-containing compounds can lead to allergies. Moreover, organohalogen compounds are poorly metabolized by the body and have a tendency to accumulate in fatty tissue.

The transition metal compounds used in the ATRP and very particularly the Cu compounds used in the overwhelming majority of polymer syntheses are likewise disadvantageous in cosmetic or personal care formulations since copper, even in low concentrations, leads to intensely colored products. Moreover, copper compounds can have an irritative and sensitizing effect on contact with the skin.

A simple and efficient method for removing the terminal halogen atoms and the transition metal compound is therefore of great interest. In particular, methods are desirable in which both take place in a simultaneous process step in order to render purification of the polymers as efficient and cost-effective as possible.

Methods for removing the terminal halogen atoms are described, inter alia, in the following places:

US 2005/0900632 discloses a method for the substitution of the halogens by means of metal alkoxides with precipitation of the metal halide formed. However, disadvantages of this procedure are the only limited availability of the metal alkoxides, their costs and the fact that the method can only be carried out after the polymers have been purified.

In Macromol. Rapid Commun., 1997, 18, pp. 1057-66, azides are used for the substitution of the halogen atoms, and in Macromol. Sci. Pure Appl. Chem., 1999, 36, pp. 653-666, phosphines are described for the substitution of the halogen atoms. However, both methods lead to incomplete conversions, are cost-intensive and toxicologically highly unacceptable. Therefore not suitable for use in cosmetic or personal care formulations. Furthermore, these methods can also only be used in a polymer-analogous reaction following product work-up.

Auke Snijder describes in his dissertation with the title "Telechelic polymers for moisture-curable coatings by ATRP" (Technical University of Eindhoven, Eindhoven, 2002) the functionalization of the polymer chain ends with OH groups through the use of mercaptoethanol. Removal of the terminal bromine atoms in this case is only to be regarded as an objective secondary effect. Thus, the reaction is described exclusively with mercaptoethanol as reagent. A substitution with unfunctionalized, or acid-, amine- or epoxy-functionalized mercaptans is not mentioned. A further difference relative to the present invention is the polymer-analogous procedure. In the described specification, the substitution reaction is only carried out after the ATRP product has been purified in a second reaction stage.

WO 00/34345 and Heuts et al. (*Macromol. Chem. Phys.,* 1999, 200, pp. 1380-1385) describe how to carry out the ATRP with the initial addition of n-dodecyl mercaptan or octyl mercaptan. In both cases, although thermally more stable, presumably halogen-free polymers are described, it is pointed out however that the breadth of the molecular weight distribution is greater than 1.6 and is thus very similar to that of the free-radically polymerized material. The advantages of the ATRP of narrow-distribution products and control of the polymer architecture are thus no longer available. Apart from that, in the procedure described, precipitation of the transition metal compounds is not mentioned.

WO 2005/098415 (U.S. Patent Application Publication 2007-193954) describes the in turn polymer-analogous substitution, i.e. carried out following purification of the polymer, of the terminal halogen atoms on polystyrenes. Here, substitution is exclusively only at one chain end with thiourea and subsequent quenching with sodium hydroxide to give sodium sulfide groups. Besides the two-stage nature, disadvantages are also the substitution only at one end, and also the implementation of the reaction following purification of the polymer.

Schön et al. (*Macromolecules,* 2001, 34, 5394-5397) describe the use of an amine ligand used in double equivalent excess relative to the copper for the substitution of the halogen by hydrogen. A disadvantage of this method is the use of a very high ligand concentration, which can discolor the product and additionally hinders the removal of copper. Moreover, the method is only described for a bulk ATRP which can barely be carried out on an industrial scale.

Methods for removing transition metal compounds from polymers or polymer solutions are described, inter alia, in the following places:

Thus, for example, low molecular weight compounds can be removed from solutions and also from solid polymers by means of extraction methods. One such process is described in general terms, for example, in WO 02/28916. However, the laid-open specification does not describe the removal of transition metal compounds. However, in order to remove transition metal complexes from a polymer solution virtually completely—i.e. below a content of 2 ppm—mere extraction is unsuitable.

A special form of extraction is aqueous liquid-liquid extraction from polymer solutions. Thus, for example in the synthesis of polyphenylene oxide, a copper catalyst is used which is removed from the polymer solution following the polymerization by aqueous extraction (cf. Ullmanns Encylopedia of Industrial Chemistry, 5th revised edition 1992, Vol. A21, p. 606 f). A disadvantage of this method is that many polar polymers can act as suspension or emulsion stabilizers and thereby prevent the two liquid phases from being able to be separated. This method can thus not be used for the work-up of polymethyl methacrylates. A further disadvantage is the only very complex transfer of such a method to industrial production scales.

On the laboratory scale, separation of the transition metal compound—for example of a copper catalyst—from polymer solutions takes place in most cases through adsorption to aluminum oxide and subsequent precipitation of the polymer in suitable precipitants or through direct precipitation without adsorption step. Suitable precipitants are, in particular, very polar solvents, such as methanol. For an appropriate ligand sphere, however, it is also possible to use particularly nonpolar precipitation media such as hexane or pentane. However, such a procedure is disadvantageous for various reasons. Firstly, following the precipitation, the polymer is not in a uniform form, such as, for example, granules. For this reason, separation and thus further work-up are difficult. Furthermore, during the precipitation process large amounts of the precipitant mixed with the solvents, the catalyst residues and further constituents to be separated off such as residual monomers are formed. These mixtures have to be separated in subsequent expensive processes. Overall, precipitation processes cannot be transferred to industrial production and are only to be used sensibly on a laboratory scale.

Moreover, methods are known in which the separation of a solid catalyst from the liquid polymer-containing solution takes place. Here, the catalyst itself becomes insoluble, for example as a result of oxidation, or it is bonded before or after the polymerization to a solid adsorbent or to a swollen, but insoluble resin. The liquid polymer-containing phase is separated from the insoluble material by filtration or centrifugation.

CN 121011 discloses a method in which an adsorbent (in particular activated carbon or aluminum oxide) is added to the polymer solution after the ATRP process and is then separated off by filtration. A disadvantage here is that complete separation is possible only by virtue of very large amounts of adsorbent.

The use of aluminum oxide is also claimed in JP 2002 363213. In JP 2005 015577, JP 2004 149563, basic or acidic silica are used. In JP 2003 096130, JP 2003 327620, JP 2004 155846, acidic, basic or combinations of hydrotalcites are used as adsorbents in mostly multistage filtration methods. Here too, large amounts of the inorganic material are used.

A disadvantage of the methods is that such adsorbents are relatively expensive and are very complex to recycle.

In DE 100 15 583 (U.S. Pat. No. 6,542,050), a ATRP method in nonpolar solvents is described where the transition metal complex is converted to an insoluble form during or after the reaction by oxidation and can be filtered off. However, such methods are only suitable for producing relatively nonpolar polymers. If polar polymers or copolymers are produced, for example polymethyl methacrylates or polysiloxane-polymethacrylate copolymers, then the polymers are insoluble in the solvent. This procedure can thus only be used to a very limited extent and in very specific polymerizations.

The person skilled in the art can easily see that all methods based on purely process-accompanying precipitation without addition of a precipitant can only lead to incomplete catalyst removal. Most prior art methods are therefore multistage methods with the addition of auxiliaries which usually function as adsorbents.

Thus, no method is known to the person skilled in the art from the prior art in which both the halogen at the chain end of the polymer and also the transition metal are removed simultaneously and as completely as possible from the polymerization solution in one simple and efficient way.

It was therefore an object of the present invention to provide a method of producing polysiloxane block copolymers which contain no covalently (organically) bonded terminal halogen, in particular no covalently bonded terminal bromine (so-called "organobromine"), and in which the transition metal used as catalyst can preferably be separated off as easily and completely as possible.

Surprisingly, it has been found that this object can be achieved by adding a mercapto-functionalized compound to the polymerization mixture obtained in the polymerization. By adding the mercaptofunctional compound, polysiloxane block copolymers are obtained which have no or only a very small amount of organically bonded, in particular terminal halogen. Furthermore, adding the mercaptofunctional compound means that the transition metal used as catalyst precipitates out, and can thus be separated off by a simple filtration.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

The present invention therefore provides polysiloxane block copolymers of the formula $A[LB(S)Q]_m$, where A is a polysiloxane block, L is a divalent organic radical which links the units A and B, B is a polymer block composed of radically polymerized monomers M, S is a sulfur atom and Q is a monovalent organic radical and m is an integer from 1 to 50, their use, and compositions which have these polysiloxane block copolymers.

The present invention likewise provides a method of producing polysiloxane block copolymers according to the invention which involves the steps A) reaction of a polysiloxane macroinitiator of the formula $A[LX]_m$, which has at least one organically bonded halogen atom X, where A is a polysiloxane block, L is a divalent organic radical and m is an integer from 1 to 50, with radically polymerizable monomers M in the presence of a catalyst exhibiting a transition metal in a polymerization step and B) addition of a compound Q-SH where Q is a monovalent, substituted or unsubstituted organic radical, to the polymerization mixture of step A).

The polysiloxane block copolymers according to the invention, a method for their production and their use are described below by way of example without any intention to restrict the invention to these exemplary embodiments. Where ranges, general formulae or compound classes are given below, these are intended to include not only the corresponding ranges or groups of compounds that are explicitly mentioned, but also all partial ranges and part groups of compounds which can be obtained by extracting individual values (ranges) or compounds. If documents are cited within the scope of the present description, then their contents should belong in their entirety to the disclosure content of the present invention.

The polysiloxane block copolymers of the formula $A[LB(S)Q]_m$ according to the invention are characterized in that A is a polysiloxane block, L is a divalent organic radical (linker) which links the units A and B, B is a polymer block composed of radically polymerizable monomers, S is a sulfur atom and Q is a substituted or unsubstituted monovalent organic radical and m is an integer from 1 to 50, preferably 2 to 10 and preferably 2, 3 or 4.

The unit A is preferably a branched or unbranched, substituted or unsubstituted polysiloxane radical which is described by formula (I).

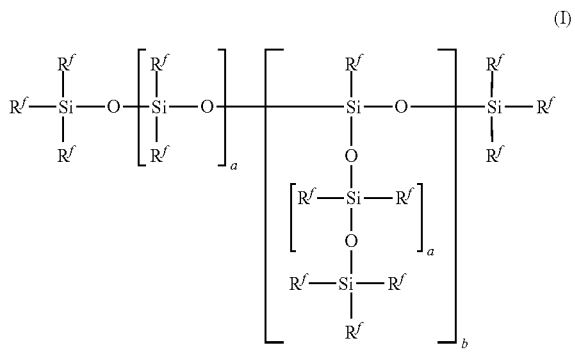

where
b is a number from 0 to 10, preferably <5 and particularly preferably 0,
a is a number from 1 to 500, preferably 1 to 250 and particularly preferably 1 to 100,
$R^f$ are identical or different radicals $R^1$ or the linking radical L, with the proviso that at least one radical $R^f$ is a radical L and preferably at most 50 radicals $R^f$ are radicals L,
$R^1$ are alkyl radicals having 1 to 18 carbon atoms, preferably 1 to 6 carbon atoms, particularly preferably methyl or an aryl radical, preferably phenyl, where the radicals $R^1$ may be substituted or unsubstituted.

The radical L can be, for example, an unbranched or branched substituted or unsubstituted organic radical, in particular hydrocarbon radical, having 1 to 60 carbon atoms, preferably 1 to 20 carbon atoms and particularly preferably 3-10 carbon atoms. The radical L can be interrupted by divalent radicals which are bonded on both sides to carbon atoms, such as, for example, —O—, —C(O)O—, CONR$^4$, NR$^4$C(O), or —C(O)—, where $R^4$ is a monovalent substituted or unsubstituted, linear or branched radical containing 1 to 18 carbon atoms. The radical L particularly preferably contains at least one —C(O) unit.

The polymer block B is composed of radically polymerizable monomers M. The radically polymerizable monomers can be selected from the radically polymerizable monomers M described below (step A)). Preferably, the polymer block B is composed of monomers selected from the group of (meth)acrylates and (meth)acrylic acids and derivatives thereof. The monomers M are particularly preferably selected from the group comprising substituted or unsubstituted (meth)acrylic acid or derivatives thereof. Preferably used monomers M include acrylic acid, methacrylic acid, ethacrylic acid, methyl acrylate, ethyl acrylate, n-butyl acrylate, isobutyl acrylate, t-butyl acrylate, 2-ethylhexyl acrylate, decyl acrylate, octyl acrylate, methyl methacrylate, ethyl methacrylate, n-butyl methacrylate, isobutyl methacrylate, t-butyl methacrylate, 2-ethylhexyl methacrylate, decyl methacrylate, octyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, octyl ethacrylate, 2,3-dihydroxypropyl acrylate, 2,3-dihydroxypropyl methacrylate, 2-hydroxyethyl acrylate, 2-hydroxypropyl acrylate, 3-hydroxypropyl acrylate, 2-hydroxyethyl methacrylate, 3-hydroxypropyl methacrylate, glyceryl monoacrylate, glyceryl monomethacrylate, glyceryl monoethacrylate, glycidyl acrylate, glycidyl methacrylate, acrylamide, methacrylamide, ethacrylamide, N-methylacrylamide, N,N-dimethylacrylamide, N,N-dimethylmethacrylamide, N-ethylacrylamide, N-isopropylacrylamide, N-butylacrylamide, N-t-butylacrylamide, N,N-di-n-butylacrylamide, N,N-diethylacrylamide, N-octylacrylamide, N-octadecylacrylamide, N,N-diethylacrylamide, N-phenylacrylamide, N-methylmethacrylamide, N-ethylmethacrylamide, N-docdecyl-methacrylamide, N,N-dimethylaminoethylacrylamide, quaternized N,N-dimethylaminoethylacrylamide, N-dimethylaminoethylmethacrylamide, quaternized N,N-dimethylaminoethylmethacrylamide, N,N-dimethylaminoethyl acrylate, N,N-dimethylaminoethyl methacrylate, quaternized N,N-dimethylaminoethyl acrylate, quaternized N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, the monoesters of maleic acid, the diesters of maleic acid, maleic anhydride, maleimide, fumaric acid, itaconic acid, the monoesters of itaconic acid, the diesters of itaconic acid, itaconic anhydride, crotonic acid, angelica acid, diallyldimethylammonium chloride, vinylpyrrolidone, vinylimidazole, methyl vinyl ether, methyl vinyl ketone, vinylpyridine, vinylfuran, styrene sulfonate, allyl alcohol, allyl citrate, allyl tartrate, vinyl acetate, vinyl alcohol, vinylcaprolactam and mixtures thereof.

The unit B preferably has a number-average molecular weight of from 1000 g/mol to 200 000 g/mol, preferably a number-average molecular weight of from 4000 g/mol to 120 000 g/mol and particularly preferably from 4000 g/mol to 75 000 g/mol.

The unit B is particularly preferably a poly(meth)acrylate unit, preferably having a number-average molecular weight of from 1000 g/mol to 200 000 g/mol, preferably having a number-average molecular weight of from 4000 g/mol to 120 000 g/mol and particularly preferably having a number-average molecular weight of from 4000 g/mol to 75 000 g/mol.

The radical Q in the polysiloxane block copolymer according to the invention is preferably an alkyl radical, an alcohol radical or an acid radical which preferably has from 1 to 20, preferably 2 to 15, carbon atoms. The radical SQ is particularly preferably a thioglycolacetic acid radical, mercaptopropionic acid radical, mercaptoethanol radical, mercaptopropanol radical, mercaptobutanol radical, mercaptohexanol radical, octyl thioglycolate radical, methyl mercaptan radical, ethyl mercaptan radical, butyl mercaptan radical, dodecyl mercaptan radical, isooctyl mercaptan radical or tert-dodecyl mercaptan radical. Here, these radicals can carry further substituents.

The polysiloxane block copolymer according to the invention preferably has a number-average molecular weight of from 5000 g/mol to 1 000 000 g/mol, preferably from 10 000 g/mol to 500 000 g/mol and very particularly preferably from 10 000 g/mol to 250 000 g/mol.

The polysiloxane block copolymer according to the invention preferably has less than 5 mass-ppm, preferably less than 2 mass-ppm, of organically bonded, in particular of terminal halogen, in particular bromine. The polysiloxane particularly preferably has no organically bonded halogen or at least only undetectable amounts of organically bonded halogen.

The polysiloxane block copolymers according to the invention can be produced in various ways. Preferably, the polysiloxane block copolymers according to the invention are obtainable by the method described below.

The method according to the invention for producing the polysiloxane block copolymers according to the invention is characterized in that it comprises the steps A) reaction of an atom transfer radical initiator, which is a polysiloxane macroinitiator of the formula $A[LX]_m$, which has at least one organically bonded halogen atom X, where A is a polysiloxane block, L is a divalent organic radical and m is an integer from 1 to 50, preferably 2 to 10 and preferably 2, 3 or 4, with radically polymerizable monomers in the presence of a catalyst having transition metal in a polymerization step and B) addition of a compound Q-SH, where Q is a monovalent organic radical, to the polymerization mixture of step A).

Step A)

Polysiloxane macroinitiators of the formula $A[LX]_m$ that can be used are all radical initiators which satisfy the formula $A[LX]_m$. Polysiloxane macroinitiators of the formula $A[LX]_m$ can be obtained, for example, by firstly reacting a suitable radical initiator with the reactive group(s) of a polysiloxane, e.g. in a nucleophilic substitution reaction.

In this reaction, the polysiloxane used is preferably a polysiloxane which has at least one functional group which has an O, N or S atom and is suitable for a nucleophilic attack at these atoms.

The polysiloxanes used for producing polysiloxane macroinitiators of the formula A[LX] may be linear, branched or hyperbranched, provided they are functionalized with at least one of the groups as described above.

Preference is given to using polysiloxanes which are selected from polysiloxanes of the formula (Ia),

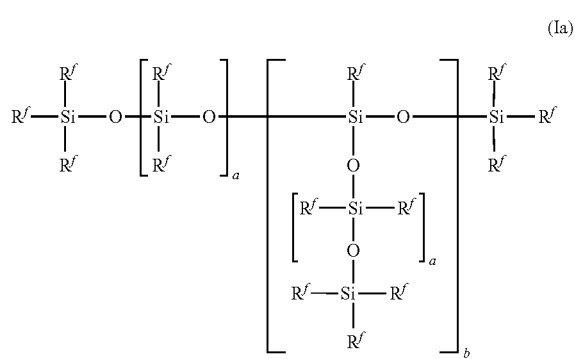

(Ia)

where b is a number from 0 to 10, preferably <5 and more preferably 0, a is a number from 1 to 500, preferably 1 to 250 and more preferably 1 to 100, $R^f$ are identical or different radicals $R^1$ or $R^2$, with the proviso that at least one radical $R^f$ is a radical $R^2$, $R^1$ are alkyl radicals having 1 to 18 carbon atoms, preferably 1 to 6 carbon atoms, or an aryl radical, preferably phenyl, where the radicals $R^1$ may be substituted or unsubstituted, $R^2$ is a radical of the general formula (II)

-T-Y (II)

T is a divalent optionally branched substituted or unsubstituted hydrocarbon radical having 1 to 60 carbon atoms, preferably 1 to 20 carbon atoms and particularly preferably 3 to 10 carbon atoms, and Y is selected from the group comprising —OH, —SH, —$NH_2$ and —$NHR^3$, where $R^3$ is a monovalent substituted or unsubstituted, linear or branched radical containing 1 to 18 carbon atoms.

The divalent radical T can be interrupted by divalent radicals which are bonded to carbon atoms on both sides, such as, for example, —O—, —C(O)O—, $CONR^4$, $NR^4C(O)$, or —C(O)—, where $R^4$ is a monovalent substituted or unsubstituted, linear or branched radical containing 1 to 18 carbon atoms.

The radical initiator used is preferably a compound which contains at least one group C(O)X, in which X is a leaving group which, in a nucleophilic attack, can be substituted by the O, N or S atom of the functional group of the polysiloxane and contains at least one organically bonded halogen atom which is capable of forming radicals in the presence of transition metal catalysts.

As radical initiators, preference is given to using compounds of the formula (III):

$R^5$—C(O)X (III)

where $R^5$ is an organic halogen group and X is the leaving group. Preferably, the leaving group is a halogen atom (F, Cl, Br, or I). The term organic halogen group is generally understood as meaning a linear, branched or cyclic (aromatic or aliphatic), substituted or unsubstituted carbon-containing structural unit which likewise contains at least one halogen atom (F, Cl, Br, or I).

As radical initiators for producing the polysiloxane macroinitiator of the formula $A[LX]_m$, particular preference is given to using compounds of the formula (IV):

$C(R^6)(R^7)Z^1-(R^8)_r$—$C(O)Z^2$ (IV)

where $Z^1$, $Z^2$ independently of one another are fluorine, chlorine, bromine or iodine, preferably bromine, where preferably $Z^1=Z^2$ and particularly preferably $Z^1=Z^2$=bromine, $R^6$, $R^7$ independently of one another are selected from the group comprising hydrogen, monovalent branched or unbranched organic radicals, in particular alkyl radicals having 1 to 18 carbon atoms, preferably 1 to 6 carbon atoms, particularly preferably 1 to 3 carbon atoms or an aryl radical, where the radicals $R^6$ and/or $R^7$ may be substituted or unsubstituted.

r is 0 or 1, preferably 0

$R^8$ is a divalent optionally branched substituted or unsubstituted organic radical, preferably alkyl radical having 1 to 20 carbon atoms.

The nucleophilic substitution reaction between functional polysiloxane and radical initiator can take place under the reaction conditions typical for such reactions which are known to the person skilled in the art.

The actual reaction in process step A) involves the reaction (polymerization) of the polysiloxane macroinitiator with radically polymerizable monomers M in the presence of a catalyst having transition metal, preferably a transition metal salt, where a polysiloxane-containing copolymer is obtained.

Process step A) can be carried out as ATRP. Here, the organic halogen group of the polysiloxane macroinitiator functions as initiator and the presence of radically polymerizable monomers M and the catalyst leads to the formation of a covalent linkage between at least one block B, formed from radically polymerized monomers, and the polysiloxane macroinitiator. This block formed from radically polymerizable monomers forms the block B of the polysiloxane copolymers according to formula $A[LB(S)Q]_m$, with the polysiloxane macroinitiator forming the block A.

Suitable catalysts for the ATRP are, for example, those transition metal compounds as are described in more detail, for example, in Chem. Rev. 2001, 101, p. 2921ff, to which reference is expressly made. In general, it is possible to use all transition metal compounds which can form a redox cycle with the initiator or the polymer chain which has a transferable atomic group, e.g. a halogen. Preferably used catalysts are selected from the copper, iron, cobalt, chromium, manganese, molybdenum, silver, zinc, palladium, rhodium, platinum, ruthenium, iridium, ytterbium, samarium, rhenium and/or nickel compounds, in particular those in which the transition metal is present in oxidation state I. Preference is given to using copper compounds. Preferably, the copper compounds used are those selected from $Cu_2O$, $CuBr$, $CuCl$, $CuI$, $CuN_3$, $CuSCN$, $CuCN$, $CuNO_2$, $CuNO_3$, $CuBF_4$, $Cu(CH_3COO)$ or $Cu(CF_3COO)$ and mixtures thereof.

Alternatively to carrying out process step A) as ATRP, step A) can also be carried out as so-called reverse ATRP. In this variant of the method, transition metal compounds can be used in higher oxidation states, such as, for example, $CuBr_2$, $CUCl_2$, $CuO$, $CrCl_3$, $Fe_2O_3$ or $FeBr_3$. In these cases, the reaction can be initiated with the help of classic radical formers, such as, for example AIBN. Here, the transition metal compounds are firstly reduced since they are reacted with the radicals produced from the classic radical formers. Reverse ATRP was described inter alia by Wang and Matyjaszewski in *Macromolecules,* 1995, 28, p. 7572 ff, to which reference is expressly made.

One variant of reverse ATRP is the additional use of metals in oxidation state zero. Through an increasing comproportionation with the transition metal compounds of the higher oxidation state, an increase in the reaction rate is brought about. This method is described in more detail in WO 98/40415 (U.S. Pat. No. 5,763,548), to which reference is expressly made.

In order to increase the solubility of the metal compounds in the reaction solution and at the same time to avoid the formation of stable and therefore polymerization-inactive organometallic compounds, it may be advantageous to add ligands to the reaction mixture. Additionally, by adding ligands, it is possible to facilitate the abstraction of the transferable atomic group by the transition metal compound. A list of suitable ligands is given, for example, in WO 97/18247, WO 97/47661 (U.S. Pat. No. 6,310,149) or WO 98/40415. Preferably, the compounds used as ligand have in most cases one or more nitrogen, oxygen, phosphorus and/or sulfur atoms as coordinative constituent. Particular preference is given here to nitrogen-containing compounds. Very particular preference is given to nitrogen-containing chelate ligands. Examples of particularly suitable ligands are, for example, 2,2'-bipyridine, N,N,N',N'',N''-pentamethyldiethylenetriamine (PMDETA), tris(2-aminoethyl)amine (TREN), N,N,N',N'-tetramethylethylenediamine or 1,1,4,7,10,10-hexamethyltriethylenetetramine. It will be appreciated by a person skilled in the art that a large number of other ligands can likewise be used.

These ligands can form coordination compounds in situ with the metal compounds, or they can firstly be produced as coordination compounds and then added to the reaction mixture.

The ratio of ligand to transition metal is dependent on the denticity of the ligand and the coordination number of the transition metal. Preferably, the amount of ligand used in process step A) is such that the molar ratio of ligand to transition metal is from 100:1 to 0.1:1, preferably 6:1 to 0.1:1 and particularly preferably 3:1 to 1:1.

The polymerization in step A) can take place without a diluent or take place in solution. The polymerization in step A) can be carried out as emulsion polymerization, miniemulsion polymerization or microemulsion polymerization or suspension polymerization.

If step A) is carried out in the presence of a solvent, then preferably halogen-free solvents, preferably toluene, xylene, acetates, preferably butyl acetate, ethyl acetate, propyl acetate; ketones, preferably ethyl methyl ketone, acetone; ether; aliphatics, preferably pentane, hexane; or alcohols, preferably cyclohexanol, butanol, hexanol, are used. Water or mixtures of water and water-miscible solvents are also suitable as solvents.

The polymerization in step A) can be carried out at atmospheric pressure, subatmospheric pressure or superatmospheric pressure, preferably at atmospheric pressure. The polymerization can be carried out in a temperature range from −20° C. to 200° C., preferably from 0° C. to 130° C., particularly preferably from 30° C. to 120° C.

The radically polymerizable monomers M used in step A) are preferably ethylenically unsaturated monomers.

"Polymerizable" monomers are understood as meaning those as described in the present invention are polymerizable using ATRP. Preferably, in the ATRP, the polymer chain length and the polymer architecture can be controlled in a known manner and it is possible to obtain narrow-distribution polymers with regard to the polydispersity of the molar mass distribution (ratio of weight-average of the molecular mass to the number-average of the molecular mass).

"Ethylenically" unsaturated monomers are understood as meaning monomers which have at least one polymerizable carbon-carbon double bond, where the double bond may be mono-, di-, tri- or tetrasubstituted. It is possible to use either individual monomers or mixtures of monomers. The monomers are preferably selected such that they correspond to the desired physical and chemical properties of the polysiloxane block copolymer.

Suitable ethylenically unsaturated monomers M which can be used for the polymerization can be described by the general formula (V):

$$H(R^9)C=C(R^{10})(C(O)G) \quad (V)$$

in which the radicals $R^9$ and $R^{10}$, independently of one another, can be selected from the group comprising hydrogen, $C_1$-$C_{10}$ unbranched or branched alkyl radicals, methoxy, ethoxy, 2-hydroxyethoxy, 2-methoxyethyl or 2-ethoxyethyl. The radical G can be selected from the group comprising— hydroxy, —$O(M)_{1/v}$, —$OR^{11}$, —$NH_2$, —$NHR^{11}$ and —$N(R^{11})(R^{12})$; where M is a counterion of valency v, selected from the group of metal ions, such as alkali metal ions, alkaline earth metal ions, ammonium ions, substituted ammonium ions, such as mono-, di-, tri- or tetraalkylammonium ions, and each radical $R^{11}$ and $R^{12}$ can independently be selected from the group comprising hydrogen, $C_1$-$C_{40}$ straight-chain or branched alkyl chains, polyether radicals, polyether amine radicals optionally substituted by one or more substituents selected from the group comprising hydroxy, amino, $C_1$-$C_3$ alkoxy, $C_1$-$C_3$ alkylamino and di($C_1$-$C_3$ alkyl)amino, e.g. N,N-dimethylamino-ethyl, 2-hydroxyethyl, 2-methoxyethyl, and 2-ethoxyethyl. Representative nonlimiting examples of monomers also include protected or unprotected acrylic acid and methacrylic acid, and also salts and esters and amides of these acids.

The salts can be derived from any desired nontoxic metal, ammonium or substituted ammonium counterion. The esters can be derived from $C_1$-$C_{40}$ straight-chain, $C_3$-$C_{40}$ branched alkyl chains or $C_3$-$C_{40}$ carbocyclic alcohols, from polyfunctional alcohols containing from 2 to 8 carbon atoms and from 2 to 8 hydroxy groups, from amino alcohols and polyethylene glycols or polypropylene glycols or other polyether radicals, and hydroxy-functionalized polyethers. (Nonlimiting examples include ethylene glycol, propylene glycol, butylene glycol, hexylene glycol, glycerol and 1,2,6-hexanetriol), of amino alcohols (nonlimiting examples include aminoethanol, dimethylaminoethanol, diethylaminoethanol and quaternized products thereof); or of ether alcohols (nonlimiting examples include methoxyethanol and ethoxyethanol).

The amides can be unsubstituted, N-alkyl or N-alkylamino monosubstituted or N,N-dialkyl or N,N-dialkylamino-disubstituted, where the alkyl or alkylamino groups are derived from $C_1$-$C_{40}$ straight-chain or $C_3$-$C_{40}$ branched or $C_3$-$C_{40}$ cyclic units. In addition, the alkylamino group can be quaternized.

Monomers that can likewise be used are protected or unprotected acrylic and/or methacrylic acids, their salts, esters and amides, where the second or third carbon position of the acrylic acids and/or methacrylic acids can, independently of one another, be substituted. The substituents can be selected from the group comprising $C_1$-$C_4$ alkyl radicals, hydroxyl, —CN, and —COOH, for example methacrylic acid, ethacrylic acid and 3-cyanoacrylic acid. The salts, esters and amides of these substituted acrylic and methacrylic acids, as described above, can likewise be used.

Furthermore, monomers M that can be used include: vinyl and allyl esters of straight-chain carboxylic acids containing 1 to 40 carbon atoms, branched carboxylic acids containing 3 to 40 carbon atoms or carbocyclic carboxylic acids containing 3 to 40 carbon atoms, pyridines substituted by at least one vinyl or allyl group (e.g. vinylpyridine or allylpyridine), hydrocarbons with at least one unsaturated carbon-carbon double bond (e.g. styrene, alpha-methylstyrene, t-butylstyrene, butadiene, isoprene, cyclohexadiene, ethylene, propylene, 1-butene, 2-butene, isobutene, para-methylstyrene) and mixtures thereof.

The radically polymerizable monomers B used are preferably substituted or unsubstituted (meth)acrylic acid or derivatives thereof. Preferably used monomers M include acrylic acid, methacrylic acid, ethacrylic acid, methyl acrylate, ethyl acrylate, n-butyl acrylate, isobutyl acrylate, t-butyl acrylate, 2-ethylhexyl acrylate, decyl acrylate, octyl acryolate, methyl methacrylate, ethyl methacrylate, n-butyl methacrylate, isobutyl methacrylate, t-butyl methacrylate, 2-ethylhexyl methacrylate, decyl methacrylate, octyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, octyl ethacrylate, 2,3-dihydroxypropyl acrylate, 2,3-dihydroxypropyl methacrylate, 2-hydroxyethyl acrylate, 2-hydroxypropyl acrylate, 3-hydroxypropyl acrylate, 2-hydroxyethyl methacrylate, 3-hydroxypropyl methacrylate, glyceryl monoacrylate, glyceryl monomethacrylate, glyceryl monoethacrylate, glycidyl acrylate, glycidyl methacrylate, acrylamide, methacrylamide, ethacrylamide, N-methylacrylamide, N,N-dimethylacrylamide, N,N-dimethylmethacrylamide, N-ethylacrylamide, N-isopropylacrylamide, N-butylacrylamide, N-t-butylacrylamide, N,N-di-n-butylacrylamide, N,N-diethylacrylamide, N-octylacrylamide, N-octadecylacrylamide, N,N-diethylacrylamide, N-phenylacrylamide, N-methylmethacrylamide, N-ethylmethacrylamide, N-dodecyl-methacrylamide, N,N-dimethylaminoethylacrylamide, quaternized N,N-dimethylaminoethylacrylamide, N-dimethylaminoethylmethacrylamide, quaternized N,N-dimethylaminoethylmethacrylamide, N,N-dimethylaminoethyl acrylate, N,N-dimethylaminoethyl methacrylate, quaternized N,N-dimethylaminoethyl acrylate, quaternized N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, the monoesters of maleic acid, the diesters of maleic acid, maleic anhydride, maleimide, fumaric acid, itaconic acid, the monoesters of itaconic acid, the diesters of itaconic acid, itaconic anhydride, crotonic acid, angelica acid, diallyldimethylammonium chloride, vinylpyrrolidones, vinylimidazole, methyl vinyl ether, methyl vinyl ketone, vinylpyridine, vinylfuran, styrenesulfonate, allyl alcohol, allyl citrate, allyl tartrate, vinyl acetate, vinyl alcohol, vinylcaprolactam and mixtures thereof.

Monomers are particularly preferably selected from the group comprising methyl acrylate, ethyl acrylate, n-butyl acrylate, isobutyl acrylate, t-butyl acrylate, 2-ethylhexyl acrylate, decyl acrylate, octyl acrylate, methyl methacrylate, ethyl methacrylate, n-butyl methacrylate, isobutyl methacrylate, t-butyl methacrylate, 2-ethylhexyl methacrylate, decyl methacrylate, octyl methacrylate, N-octylacrylamide, 2-methoxyethyl acrylate, 2-hydroxyethyl acrylate, N,N-dimethylaminoethyl acrylate, N,N-dimethylaminoethyl methacrylate, 2-hydroxyethyl methacrylate and mixtures thereof.

Very particular preference is given to monomers selected from the group comprising methyl acrylate, methyl methacrylate, n-butyl acrylate, n-butyl methacrylate, N,N-dimethylaminoethyl acrylate, N,N-dimethylaminoethyl methacrylate, 2-hydroxyethyl methacrylate and mixtures thereof.

The polymerization in the ATRP can be terminated, for example, as known to the person skilled in the art through oxidation of the transition metal. This can happen, for example, by passing oxygen, e.g. by passing through air, into the polymerization mixture.

Step B)

The addition of the sulfur compound Q-SH to the polymerization mixture of step A) can take place, for example, after or during termination of the polymerization reaction. The addition of the compound Q-SH can take place directly, or it is possible to add a suitable compound from which a compound Q-SH is obtained or released.

The sulfur compound Q-SH can be added directly to the polymerization mixture obtained in polymerization step A) or else to a worked-up polymerization mixture. Preferably, the addition takes place directly to the polymerization mixture obtained in process step A) without prior work-up.

The sulfur compound Q-SH is used, based on the chain ends (organically bonded halogen), only in a minimum excess of 1.6 equivalents, preferably 1.2 equivalents and particularly preferably from 1 to 1.1 equivalents. As a result of adding the mercaptofunctionalized sulfur compound, removal of the terminal halogen atoms presumably takes place through substitution of the same. Moreover, in the same step the transition metal compound is precipitated such that it can be separated off from the polymer solution in a simple filtration. This minimal excess leads to a per se only very low residual sulfur content in the polymer solution, which can be readily removed through modification of the following filtration step, by, for example, adding adsorbents such as activated carbon to the mixture or using an activated carbon filter as filter material.

Through the at least equivalent addition of sulfur compounds Q-SH, it is possible to obtain the polysiloxane block copolymers according to the invention which are halogen-free or virtually halogen-free. Furthermore, this step means that it is possible to obtain polysiloxane block copolymers with terminal thioether groups with a copper content of <5 mass-ppm, particularly preferably <2 mass-ppm.

The sulfur compounds Q-SH can have one or more SH groups. The sulfur compounds Q-SH preferably used in the method according to the invention are thioglycolacetic acid, mercaptopropionic acid, mercaptoethanol, mercaptopropanol, mercaptobutanol, mercaptohexanol, octyl thioglycolate, methyl mercaptan, ethyl mercaptan, butyl mercaptan, dodecyl mercaptan, isooctyl mercaptan or tert-dodecyl mercaptan.

It is easy for the person skilled in the art to see that the described sulfur compounds, when added to the polymer solution, can have no further influence on the polymers following termination of the polymerization with the exception of the described substitution reaction of the terminal halogen atoms. This applies in particular for the molecular weight distributions, the number-average molecular weight of the units A and B, additional functionalities, glass transition temperatures, and melting temperatures in the case of partially crystalline polymers and polymer architectures, such as branches or block structures.

Compositions according to the invention are characterized in that they have at least one polysiloxane block copolymer according to the invention. The compositions according to the invention may be, for example, cosmetic compositions or personal care compositions.

The compositions according to the invention can be used, for example, for the treatment of hair, as conditioners for hair treatment compositions, as hair aftertreatment compositions and for improving hair structure. In particular, the compositions according to the invention can be used for treating hair, in particular for application as hair conditioners. However, the polysiloxane block copolymers according to the invention can also be used in a wide range of different product types, such as, for example, hairspray compositions, hairstyling compositions, mousse, gels, lotions, sprays, shampoos, rinses, hand and body lotions, face moisturizers, suncream, antiacne formulations, antiaging formulations, topical analgesics, mascara and the like, the list being exemplary and not exhaustive. The carrier substances and additional components which are required in order to formulate such products vary with the product type and can be readily selected by the person skilled in the art. The text below describes some possible carrier substances and additional components which may be present in compositions according to the invention.

Carrier Substances:

The compositions according to the invention can comprise, for example, a carrier or a mixture of different carriers which are suitable for use on hair. The content of carrier in the formulation is from 0.5% by weight to 99.5% by weight, preferably from 5.0% by weight to 99.5% by weight, particularly preferably from 10.0% by weight to 98% by weight. The expression "suitable for use on hair" means that the carrier does not damage the hair, the esthetic appearance of the hair is not adversely affected or does not produce irritations on the underlying skin. Suitable carriers for the application of haircare compositions in the present invention include, for example, those which are used in hairsprays, mousse, tonics, gels, shampoos, conditioners or rinses. The choice of the suitable carrier depends on the block copolymer used and whether the formulated product is to remain on the surface to which it has been applied (e.g. hairspray, mousse, tonic or gel) or whether it is rinsed off again following application (e.g. shampoo, conditioner, rinses).

The carriers used can comprise a wide range of compounds customarily used in compositions for haircare. The carriers can comprise a solvent in order to dissolve or disperse the copolymer used, with water, $C_1$-$C_6$ alcohols, alkyl acetates with alkyl radicals which comprise one to ten carbon atoms, and mixtures thereof, being preferred. The carriers can comprise a further range of additional substances, such as acetone, hydrocarbons (e.g.: isobutane, pentane, hexane, decene), halogenated hydrocarbons (such as, for example, freons) and volatile silicone derivatives, such as, for example, cyclomethicone. If the formulation is a haircare composition, such as, for example, a hairspray, tonic, gel or mousse, the preferred solvents comprise water, ethanol, volatile silicone derivatives and mixtures thereof. The solvents which are used in such mixtures may be miscible or immiscible with one another. Mousses and aerosol hairsprays can likewise comprise any conventional propellant in order to apply the material as foam (in the case of mousse) or as a fine, uniform spray (in the case of aerosol hairspray). Examples of suitable propellants include materials from the group comprising trichlorofluoromethane, dichlorodifluoro-methane, difluoroethane, dimethyl ether, propane, n-butane or isobutane or mixtures thereof. A tonic or hairspray product with a low viscosity can also comprise an emulsifier. Examples of suitable emulsifiers include nonionic, cationic, anionic surfactants or mixtures thereof. If such an emulsifier is used, the composition comprises the emulsifier in a concentration of from 0.01% to 7.5%. The content of propellant can be adjusted as desired, but is generally between 3% and 30% for mousse compositions and from 15% to 50% in aerosol hairsprays.

Suitable containers for spraying are well known to the person skilled in the art and include conventional non-aerosol pump sprays, i.e. atomizers, aerosol containers or cans with propellants, as described above, and also pump aerosol containers which use compressed air as propellant.

If the (haircare) composition according to the invention is a conditioner or a rinse, the carrier can comprise a great diversity of conditioning compounds. If the haircare compositions are shampoos, the carrier can comprise surfactants, suspension auxiliaries and thickeners.

The carrier can have various appearances, e.g. the carrier can be an emulsion, which includes, for example, oil-in-water emulsions, water-in-oil emulsions, water-in-oil-in-water and oil-in-water-in-silicone emulsions. The viscosity of the emulsions can cover a range from 100 cps to 200 000 cps. These emulsions can also be sprayed using either mechanical pump containers or aerosol containers under superatmospheric pressure containing customary propellants. The carriers can also be applied in the form of mousse. Other suitable topical carriers include nonaqueous liquid solvents, such as oils, alcohols and silicones (e.g. mineral oil, ethanol, isopropanol, dimethicone, cyclomethicone and the like), water-based liquid single-phase solvents (e.g. water/alcohol solvent systems) and thickened variants of these nonaqueous and water-based liquid monophase solvents (e.g. where the viscosity of the solvent has been increased to a solid or a semisolid substance through the addition of suitable gum, waxes, resins, polymers, salts and similar substances.

Additional Components:

A great diversity of additional components can be used in the compositions according to the invention, in particular in the inventive cosmetic and personal care compositions of the present invention. Examples include, inter alia, but not exclusively:

Sunscreens, such as, for example, 2-ethylhexyl p-methoxycinnamate, 2-ethyl-N,N-dimethyl p-aminobenzoate, p-aminobenzoic acid, 2-phenyl-benzimidazole-5-sulfonic acid, octocrylene, oxybenzone, homomethyl salicylate, octyl salicylate, 4,4'-methoxy-t-butyldibenzoylmethane, 4-isopropyl-dibenzoylmethane, 3-benzylidenecamphor, 3-(4-methyl-benzylidene)camphor, titanium dioxide, zinc oxide, silica, iron oxide and mixtures thereof.

Antidandruff active ingredients, such as bis(2-pyridylthio) zinc 1,1'-dioxide, piroctone, selenium disulfide, sulfur, coal tar and the like.

Conditioners for haircare compositions, such as hydrocarbons, liquid silicones, and cationic materials. The hydrocarbons can be unbranched or branched and contain between 10 and 16 carbon atoms, preferably between 12 and 16 carbon atoms. Examples of suitable hydrocarbons are decane, dodecane, tetradecane, tridecane and mixtures thereof. Examples of silicone-containing conditioners include, inter alia, cyclic or linear polydimethylsiloxanes, phenyl- and alkylphenylsilicones and silicone polyols. Cationic conditioners that can be used in the compositions include quaternary ammonium salts or the salts of fatty acid amines.

Surfactants for hair shampoos and conditioner compositions. For a shampoo, the content of surfactants is preferably from 10% to 30% and particularly preferably from 12% to 25% of the composition. For conditioners, the preferred content of surfactants is from about 0.2% to 3%. The surfactants that can be used in the compositions include anionic, nonionic, zwitterionic, cationic and amphoteric surfactants.

Polymeric thickeners with carboxylic acid groups. These crosslinked or uncrosslinked polymers comprise one or more derivatives of acrylic acid, substituted acrylic acid, salts and esters of these acrylic acids and substituted acrylic acids, where, in the case of crosslinked polymers, the crosslinking agent contains two or more carbon-carbon double bonds. Examples of polymeric thickeners are those selected from the group comprising carbomers, acrylates/$C_{10}$-$C_{30}$ alkyl acrylates crosslinked copolymers and mixtures thereof. Compositions of the present invention can comprise from 0.025% to 1%, preferably from 0.05% to 0.75% and particularly preferably from 0.10% to 0.50%, of the polymeric thickeners with carboxylic acid groups.

Emulsifiers for emulsifying the large variety of carrier substances described in compositions in this invention. Suitable emulsifier types include polyethylene glycol 20 sorbitan monolaurate (polysorbate 20), polyethylene glycol 5 soya sterol, steareth-20, ceteareth-20, PPG-2 methylglucose ether distearate, ceteth-10, polysorbate 80, cetyl phosphate, potassium cetyl phosphate, diethanolaminecetyl phosphate, polysorbate 60, glyceryl stearate, PEG-100 stearate and mixtures thereof. The emulsifiers can be used individually or as a mixture of two or more emulsifiers. The cosmetic or personal care composition can comprise an emulsifier content of from 0.15 to 10%, preferably from 1% to 7% and particularly preferably from 1% to 5%.

Vitamins and derivatives thereof (e.g. ascorbic acid, vitamin E, tocopherol acetate, retinol acid, retinol, retinoids and the like)

Cationic polymers (e.g. cationic guar derivatives, such as, for example, guarhydroxypropyltrimonium chloride and hydroxypropylguarhydroxypropyltrimonium chloride, available under the trade name Jaguar C from Rhone-Poulenc, quaternary ammonium salts of hydroxyethyl cellulose, for example Polyquaternium-10, available under the trade name Ucare Polymer JR/LR/LK/KG fro, Amerchol Corp.))

Preservatives, antioxidants, chelating agents and complexing agents, pearlizing agents, esthetic components such as perfume, fragrances, dyes, pigments, hair nutrients, and essential oils.

Additives which are obvious to the person skilled in the art, but are not listed here in more detail.

The examples given below describe the present invention by way of example, without any intention to restrict the invention, the scope of application of which arises from the entire description and the claims, to the embodiments specified in the examples.

EXAMPLE 1

102.8 g of n-butyl acrylate, 6.3 g of dimethylaminoethyl methacrylate, 145.6 g of butyl acetate, 2.1 g of copper(I) oxide and 5.4 g of PMDETA (N,N,N',N'',N''-pentamethyldiethylenetriamine) were initially introduced, under an $N_2$ atmosphere, into a three-neck flask fitted with stirrer, thermometer, reflux condenser, nitrogen inlet tube and dropping funnel. The solution was stirred for 15 min at 80° C. Then, at the same temperature, 56.0 g of the macroinitiator of the formula (VI) where n=28 were added.

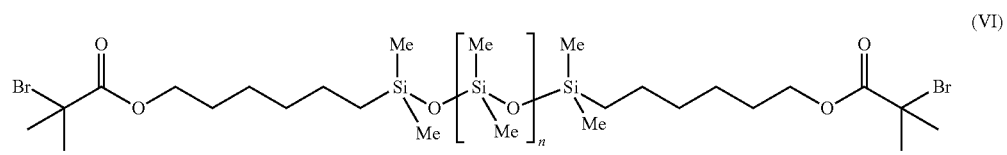

(VI)

The person skilled in the art is aware that the above-stated formula (VI) is an idealized structural formula. Higher and lower homologs are additionally present in the product.

Stirring was carried out for a polymerization time of 4 hours at 80° C. Atmospheric oxygen was then introduced for about 15 min to terminate the reaction, and 5.7 g of n-dodecyl mercaptan were added. The previously green solution spontaneously turned red and a red precipitate was formed. The precipitate was filtered off by means of filtration at superatmospheric pressure through a filter from Beko (model: KD-10). In a rotary evaporator, the solvent was drawn off from the pale yellow filtrate at a temperature of 100° C. and 2 mbar. The pale yellow, viscous residue is the desired product.
Analysis:

Copper content: <1 mass ppm (measured by means of ICP-OES on an instrument of the ACTIVA brand from Horiba Jobin Yvon)

Organobromine content: <2 mass ppm (following chemical digestion of the polymer and determination of the bromide content via ion chromatography)

EXAMPLE 2

74.4 g of n-lauryl methacrylate, 4.6 g of dimethylaminoethyl methacrylate, 150.0 g of butyl acetate, 3.1 g of copper(I) oxide and 7.9 g of PMDETA (N,N,N',N'',N''-pentamethyldiethylenetriamine) were initially introduced, under an $N_2$ atmosphere, into a three-neck flask fitted with stirrer, thermometer, reflux condenser, nitrogen inlet tube and dropping funnel. The solution was stirred for 15 min at 80° C. Then, at the same temperature, 60.0 g of the macro-initiator of the formula (VI) where n=28 were added.

Stirring was carried out for a polymerization time of 5 hours at 80° C. Atmospheric oxygen was then introduced for about 15 min to terminate the reaction, and 8.0 g of n-dodecyl mercaptan were added. The previously greenish solution spontaneously turned red and a red precipitate was formed. The precipitate was filtered off by means of filtration under superatmospheric pressure through a filter from Beko (model: KD-10). The solvent was drawn off from the pale yellow filtrate in a rotary evaporator at a temperature of 100° C. and 2 mbar. The pale yellow, viscous residue is the desired product.
Analysis:
Copper content: <1 mass ppm (measured by means of ICP-OES on an instrument of the ACTIVA brand from Horiba Jobin Yvon)
Organobromine content: <2 mass ppm (following chemical digestion of the polymer and determination of the bromide content via ion chromatography)

EXAMPLE 3

81.3 g of n-butyl acrylate, 10.0 g of dimethylaminoethyl methacrylate, 147.0 g of butyl acetate, 1.8 g of copper(I) oxide and 4.5 g of PMDETA (N,N,N',N'',N''-pentamethyl-diethylenetriamine) were initially introduced, under an $N_2$ atmosphere, into a three-neck flask fitted with stirrer, thermometer, reflux condenser, nitrogen inlet tube and dropping funnel. The solution was stirred for 15 min at 80° C. Then, at the same temperature, 60.0 g of the macro-initiator of the formula (VI) where n=48 were added.

Stirring was carried out for a polymerization time of 4 hours at 80° C. Atmospheric oxygen was then introduced for about 15 min to terminate the reaction, and 4.5 g of n-dodecyl mercaptan were added. The previously greenish solution spontaneously turned red and a red precipitate was formed. The precipitate was filtered off by means of filtration under superatmospheric pressure through a filter from Beko (model: KD-10). The solvent was drawn off from the pale yellow filtrate in a rotary evaporator at a temperature of 100° C. and 2 mbar. The pale yellow, viscous residue is the desired product.
Analysis:
Copper content: <1 mass ppm (measured by means of ICP-OES on an instrument of the ACTIVA brand from Horiba Jobin Yvon)
Organobromine content: <2 mass ppm (following chemical digestion of the polymer and determination of the bromide content via ion chromatography)

EXAMPLE 4

55.2 g of n-butyl acrylate, 6.8 g of dimethylaminoethyl methacrylate, 150.0 g of butyl acetate, 1.2 g of copper(I) oxide and 3.1 g of PMDETA (N,N,N',N'',N''-pentamethyl-diethylenetriamine) were initially introduced, under an $N_2$ atmosphere, into a three-neck flask fitted with stirrer, thermometer, reflux condenser, nitrogen inlet tube and dropping funnel. The solution was stirred for 15 min at 80° C. Then, at the same temperature, 60.0 g of the macro-initiator of the formula (VI) where n=133 were added.

Stirring was carried out for a polymerization time of 4 hours at 80° C. Then, 3.1 g of n-dodecyl mercaptan were added for about 15 min. The previously greenish solution spontaneously turned red and a red precipitate was formed. The precipitate was filtered off by means of filtration under superatmospheric pressure through a filter from Beko (model: KD-10). The solvent was drawn off from the pale yellow filtrate in a rotary evaporator at a temperature of 100° C. and 2 mbar. The pale yellow, viscous residue is the desired product.
Analysis:
Copper content: <1 mass ppm (measured by means of ICP-OES on an instrument of the ACTIVA brand from Horiba Jobin Yvon)
Organobromine content: <2 mass ppm (following chemical digestion of the polymer and determination of the bromide content via ion chromatography)

EXAMPLE 5

81.1 g of n-butyl acrylate, 5.0 g of dimethylaminoethyl methacrylate, 140.0 g of butyl acetate, 1.8 g of copper(I) oxide and 4.4 g of PMDETA (N,N,N',N'',N''-pentamethyl-diethylenetriamine) were initially introduced, under an $N_2$ atmosphere, into a three-neck flask fitted with stirrer, thermometer, reflux condenser, nitrogen inlet tube and dropping funnel. The solution was stirred for 15 min at 80° C. Then, at the same temperature, 53.2 g of the macro-initiator of the formula (VII) where n 20 were added.

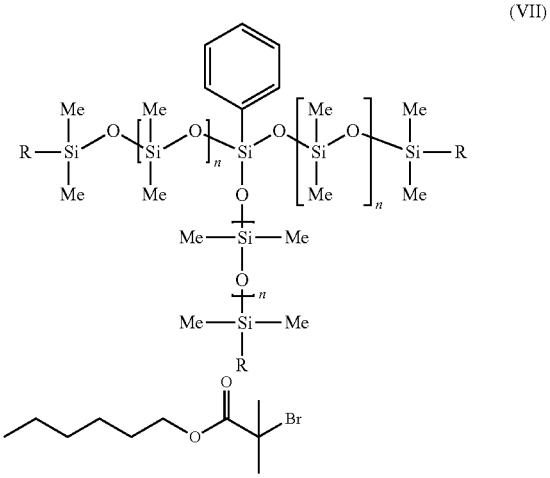

(VII)

Stirring was carried out for a polymerization time of 4 hours at 80° C. Then, 4.4 g of n-dodecyl mercaptan were added for about 15 min. The previously greenish solution spontaneously turned red and a red precipitate was formed. The precipitate was filtered off by means of filtration under superatmospheric pressure through a filter from Beko (model: KD-10). The solvent was drawn off from the pale yellow filtrate in a rotary evaporator at a temperature of 100° C. and 2 mbar. The pale yellow, viscous residue is the desired product.
Analysis:
Copper content: <1 mass ppm (measured by means of ICP-OES on an instrument of the ACTIVA brand from Horiba Jobin Yvon)
Organobromine content: <2 mass ppm (following chemical digestion of the polymer and determination of the bromide content via ion chromatography)

EXAMPLE 6

33.1 g of n-butyl acrylate, 4.1 g of dimethylaminoethyl methacrylate, 150 g of butyl acetate, 2.9 g of copper(I) oxide and 7.4 g of PMDETA (N,N,N',N'',N''-pentamethyl-diethylenetriamine) were initially introduced, under an $N_2$ atmosphere, into a three-neck flask fitted with stirrer, thermometer, reflux condenser, nitrogen inlet tube and dropping funnel. The solution was stirred for 15 min at 80° C. Then, at the same temperature, 102.4 g of the macro-initiator of the formula (VI) where n=68 were added.

Stirring was carried out for a polymerization time of 4 hours at 80° C. Atmospheric oxygen was then introduced for about 15 min to terminate the reaction, and 7.5 g of n-dodecyl mercaptan were added. The previously greenish solution spontaneously turned red and a red precipitate was formed. The precipitate was filtered off by means of filtration under superatmospheric pressure through a filter from Beko (model: KD-10). The solvent was drawn off from the pale yellow filtrate in a rotary evaporator at a temperature of 100° C. and 2 mbar. The pale yellow, viscous residue is the desired product.

Analysis:

Copper content: <2 mass ppm (measured by means of ICP-OES on an instrument of the ACTIVA brand from Horiba Jobin Yvon)

Organobromine content: <3 mass ppm (following chemical digestion of the polymer and determination of the bromide content via ion chromatography)

Applications as Hair Conditioners

For the applications-related assessment, hair tresses which are used for sensory tests are predamaged in a standardized manner by a permanent wave treatment and a bleaching treatment. Products customary in hairdressing are used for this purpose. The test procedure, the base materials used and also the details of the assessment criteria are described in DE 103 27 871.

Test Formulation:

The polysiloxane copolymers were tested in a simple hair rinse with the composition given in table 1.

TABLE 1

| Composition of the test formulations | |
|---|---|
| Product | Fractions by weight |
| TEGINACID ® C Ceteareth-25 | 0.5% |
| TEGO ® Alkanol 16 Cetyl Alcohol | 2.0% |
| Polysiloxane block copolymer ("conditioner") | 1.0% |
| Water | ad 100% |
| Citric acid | ad pH 4.0 ± 0.3 |

The polysiloxane block copolymers described in examples 1 to 5 are referred to as "conditioners".

Standardized treatment of predamaged hair tresses with conditioning samples:

The hair tresses predamaged as described above were treated as follows with the above-described conditioning rinse:

The hair tresses were wetted under running warm water. The excess water was gently squeezed out by hand, then the rinse was applied and gently worked into the hair (1 ml/hair tress (2 g)). After a residence time of 1 min, the hair was rinsed for 1 min.

Prior to the sensory assessment, the hair was dried in the air at 50% atmospheric humidity and 25° C. for at least 12 h.

In order to avoid the test results being influenced by (normally present) formulation constituents, the composition of the test formulation is intentionally chosen to be simple. Besides the specified ingredients and/or instead of the specified ingredients, formulations according to the invention can also comprise further ingredients. In particular, the combination with further ingredients can lead to a synergistic improvement in the conditioning effect. Such ingredients are described above.

Assessment Criteria

The sensory evaluations were made according to grades which were awarded on a scale from 1 to 5, with 1 being the poorest evaluation and 5 being the best evaluation. The individual test criteria each received their own evaluation. The test criteria are: detangling, wet combability, wet feel, dry combability, dry feel, shine, volume.

The results of the test of the conditioning properties of the polysiloxane block copolymers are given in table 2. The control sample comprised no polysiloxane block copolymer according to the invention.

In the sensory test, the polysiloxane block copolymers have hair conditioning properties. They are significantly better than the comparison value for the control without conditioner.

TABLE 2

Conditioning properties of the polysiloxane block copolymers

| Conditioner | Detangling | Wet combability | Wet feel | Dry combability | Dry feel | Shine | Volume |
|---|---|---|---|---|---|---|---|
| From Example 1 | 3.0 | 3.0 | 2.75 | 3.0 | 2.5 | 3.5 | 3.5 |
| From Example 2 | 3.0 | 3.25 | 3.0 | 3.25 | 3.0 | 3.25 | 3.5 |
| From Example 3 | 3.25 | 3.5 | 3.25 | 3.0 | 3.25 | 3.0 | 3.0 |
| From Example 4 | 3.0 | 3.25 | 2.75 | 3.0 | 3.0 | 3.0 | 3.25 |
| From Example 5 | 3.5 | 3.5 | 2.5 | 3.25 | 3.0 | 3.5 | 3.25 |
| Control (placebo) | 1.5 | 2.0 | 1.5 | 2.0 | 2.25 | 3.0 | 2.0 |

Formulation as Hairspray:

The polysiloxane block copolymer from example 6 was incorporated into a formulation for a non-aerosol hairspray with 80% mass fraction of volatile organic compounds (so-called 80% VOC non-aerosol hairspray) according to the composition listed in table 3.

TABLE 3

Formulation of an 80% VOC non-aerosol hairspray

| Component | Fraction in % by wt. |
|---|---|
| RESYN 28-2930 Polymer | 5 |
| AMP-95 | 0.49 |
| Polysiloxane block copolymer from Example 6 | 4.5 |
| ABIL B 8843 | 0.2 |
| Deionized water | 13.81 |
| SD Alcohol 40 | 80 |

RESYN 28-293 polymer: (INCI name: VA/Crotonates/Vinyl Neodecanoate Copolymer) is a product of National Starch.
AMP-95: (INCI name: Aminomethyl Propanol) is a product from ANGUS Chemical Company.
ABIL B 8843: (INCI name: PEG-14 Dimethicone) is a product of Goldschmidt GmbH.
SD Alcohol 40: Ethanol.

The formulation from table 3 exhibited, following application as hairspray, better flexibility of the treated hair and produced a perceptibly better feel than a formulation which comprised no polysiloxane block copolymer according to the invention.

Formulation as Hairstyling Gel:

The polysiloxane block copolymer from example 6 was incorporated into a formulation for a hairstyling gel according to the composition listed in table 4.

TABLE 4

Formulation of a hairstyling gel:

| Component | Fraction in % by wt. |
|---|---|
| AMP-95 | 0.8 |
| Polysiloxane block copolymer from example 6 | 2 |
| Deionized water | 86.4 |
| SD Alcohol 40 | 10 |
| Carbopol ETD 2020 | 0.8 |

AMP-95: (INCI name: Aminomethyl Propanol) is a product from Angus.
Carbopol ETD 2020: (INCI name: Acrylates/C10-30 Alkyl Acrylate Crosspolymer) is a product from Noveon.

The formulation from table 4 forms a gel with a pudding-like consistency which, upon application as styling gel, leads to adequate stability in the hair coupled with simultaneous flexibility and pleasant feel.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A polysiloxane block copolymer of the formula A[LB(S)Q]$_m$ where A is a polysiloxane block, L is a divalent organic radical which links the units A and B, B is a polymer block composed of radically polymerized monomers M, S is a sulfur atom and Q is a monovalent organic radical and m is an integer from 1 to 50.

2. The polysiloxane block copolymer as claimed in claim 1, wherein A is a branched or unbranched, substituted or unsubstituted polysiloxane radical which is described by formula (I)

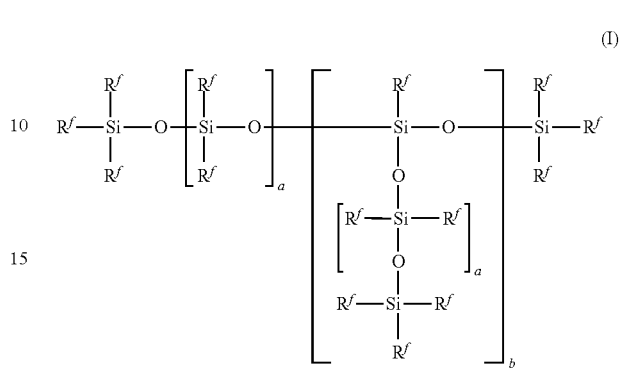

where
b is a number from 0 to 10,
a is a number from 1 to 500,
R$^f$ are identical or different radicals R$^1$ or the linking radical L, with the proviso that at least one radical R$^f$ is a radical L and at most 50 radicals R$^f$ are radicals L, and
R$^1$ are alkyl radicals having 1 to 18 carbon atoms, where the radicals R$^1$ may be substituted or unsubstituted.

3. The polysiloxane block copolymer as claimed in claim 1, wherein L is a branched or unbranched, substituted or unsubstituted hydrocarbon radical having 1 to 60 carbon atoms which has at least one unit —C(O)—.

4. The polysiloxane block copolymer as claimed in claim 1, wherein B is a poly(meth)acrylate unit with a number-average molecular weight of from 1000 g/mol to 200 000 g/mol.

5. The polysiloxane block copolymer as claimed in claim 1, wherein Q is an alkyl radical, an alcohol radical or an acid radical, preferably having 1 to 20 carbon atoms.

6. The polysiloxane block copolymer as claimed in claim 1, wherein the block copolymer has a number-average molecular weight of from 5000 g/mol to 1 000 000 g/mol.

7. The polysiloxane block copolymer as claimed in claim 1, wherein the block copolymer has less than 5 mass-ppm of terminal halogens.

8. The polysiloxane block copolymer as claimed in claim 2, wherein:
L is a branched or unbranched, substituted or unsubstituted hydrocarbon radical having 1 to 60 carbon atoms which has at least one unit —C(O)—;
B is a poly(meth)acrylate unit with a number-average molecular weight of from 1000 g/mol to 200 000 g/mol;
Q is an alkyl radical, an alcohol radical or an acid radical, preferably having 1 to 20 carbon atoms;
the block copolymer has a number-average molecular weight of from 5000 g/mol to 1 000 000 g/mol; and
the block copolymer has less than 5 mass-ppm of terminal halogens.

9. A method of producing polysiloxane block copolymers as claimed in claim 1, which comprises the steps
A) reaction of an atom transfer radical initiator, which is a polysiloxane macroinitiator of the formula A[LX]$_m$, which has at least one organically bonded halogen atom X, where A is a polysiloxane block, L is a divalent organic radical and m is an integer from 1 to 50, with radically polymerizable monomers M in the presence of a catalyst having transition metal in a polymerization step and B) addition of a compound Q-SH, where Q is a monovalent organic radical, to the polymerization mixture of step A).

10. The method as claimed in claim 9, wherein substituted or unsubstituted (meth)acrylic acid or derivatives thereof are used as radically polymerizable monomers.

11. The method as claimed in claim 9, wherein thioglycolacetic acid, mercaptopropionic acid, mercaptoethanol, mercaptopropanol, mercaptobutanol, mercaptohexanol, octyl thioglycolate, methyl mercaptan, ethyl mercaptan, butyl mercaptan, dodecyl mercaptan, isooctyl mercaptan or tert-dodecyl mercaptan is used as compound Q-SH.

12. A composition comprising at least one polysiloxane block copolymer as claimed in claim 1.

13. The composition as claimed in claim 12, wherein the composition is a cosmetic composition or a personal care composition.

14. A method of treating and/or conditioning hair which comprises administering the composition as claimed in claim 12 to the hair of a person in need thereof.

* * * * *